US007560073B1

(12) United States Patent
Peters et al.

(10) Patent No.: US 7,560,073 B1

(45) Date of Patent: Jul. 14, 2009

(54) SAMPLE SUPPORT

(75) Inventors: Ralf-Peter Peters, Bergisch-Gladbach (DE); Nezih Ünal, Wuppertal (DE); Dirk Klaus Osterloh, Dortmund (DE); Herbert Backes, Remagen-Unkelbach (DE)

(73) Assignees: Boehringer Ingelheim Microparts GmbH, Dortmund (DE); Merlin Lilliput GmbH, Bornheim-Hersel (DE)

( * ) Notice: Subject to any disclaimer, the term of this patent is extended or adjusted under 35 U.S.C. 154(b) by 0 days.

(21) Appl. No.: 09/623,910

(22) PCT Filed: Mar. 11, 1999

(86) PCT No.: PCT/EP99/01607

§ 371 (c)(1), (2), (4) Date: Nov. 13, 2000

(87) PCT Pub. No.: WO99/46045

PCT Pub. Date: Sep. 16, 1999

(30) Foreign Application Priority Data

Mar. 11, 1998 (DE) ................................ 198 10 499
Jan. 21, 1999 (DE) ................................ 199 02 309

(51) Int. Cl.
*C12M 1/22* (2006.01)

(52) U.S. Cl. ......................... 422/99; 422/101; 422/102; 435/287.3; 435/288.5; 435/305.2

(58) Field of Classification Search ........... 422/99-102; 435/29, 30, 33, 40, 287.3, 288.5, 288.7, 305.2
See application file for complete search history.

(56) References Cited

U.S. PATENT DOCUMENTS 4,038,151 A 7/1977 Fadler et al.
4,426,451 A 1/1984 Columbus
4,963,498 A * 10/1990 Hillman et al. ............... 436/69
5,223,219 A 6/1993 Subramanian et al.
5,230,866 A 7/1993 Shartle et al.
5,637,469 A * 6/1997 Wilding et al. ............. 435/7.21
5,670,375 A 9/1997 Seaton et al.
5,800,785 A * 9/1998 Bochner ..................... 422/101
5,922,593 A * 7/1999 Livingston .................. 422/100
5,948,673 A * 9/1999 Cottingham ................. 422/50
7,094,354 B2 * 8/2006 Pugia et al. ................. 210/787

FOREIGN PATENT DOCUMENTS

EP A2282840 9/1988
FR A1-2657879 8/1991

* cited by examiner

*Primary Examiner*—Lyle A Alexander
(74) *Attorney, Agent, or Firm*—Birch, Stewart, Kolasch & Birch, LLP

(57) ABSTRACT

The comprises at least one sample receiving chamber for a sample liquid, and a distributor channel for sample liquid connected to said at least one sample receiving chamber, with at least one such distributor channel extending from each sample receiving chamber. The sample support further comprises at least one reaction chamber entered by an inflow channel branched off said at least one distributor channel, and a venting opening for each reaction chamber. Each distributor channel and each inflow channel are dimensioned to have the liquid transport through the distributor and inflow channels effected by capillary forces. In each reaction chamber, the entrance region of the inflow channel is provided with a means for generating a capillary force causing the sample liquid to flow from the inflow channel into the reaction chamber.

9 Claims, 6 Drawing Sheets

FIG.11
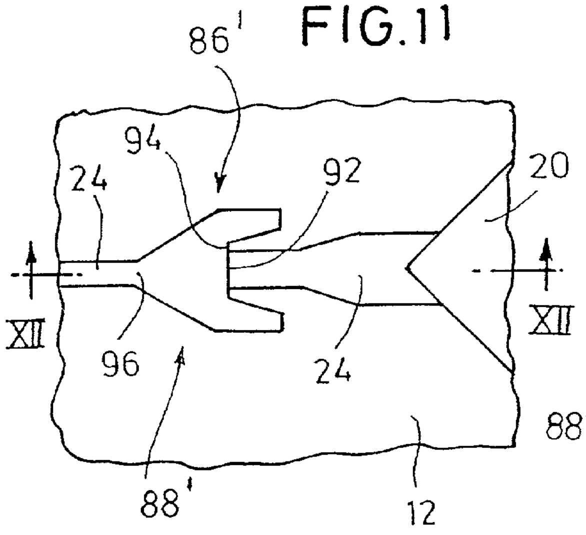
FIG.12
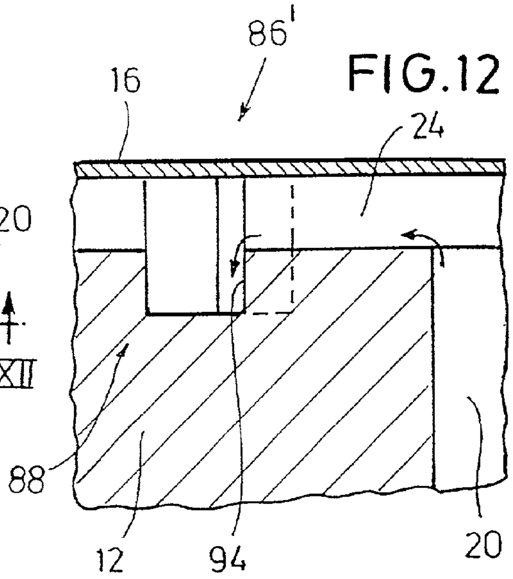
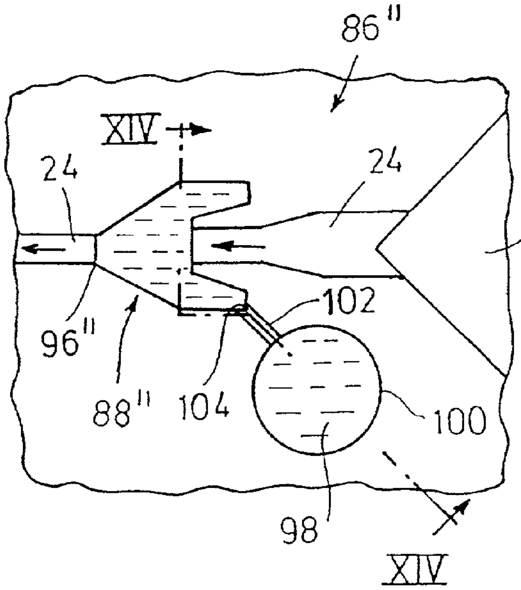
FIG.13
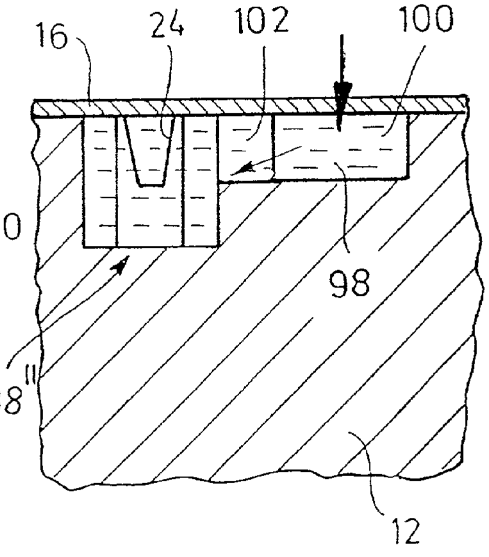
FIG.14

SAMPLE SUPPORT

This application is the national phase under 35 U.S.C. § 371 of PCT International Application No. PCT/EP99/01607 which has an International filing date of Mar. 11, 1999, which designated the United States of America.

The invention relates to a sample support of the type used for microbiological examinations performed on sample liquids as well as for medical and environmental analysis and diagnostics.

In microbiological diagnostics, use is made of optical methods such as absorption, scattering and luminescence analyses, e.g. for transmission, fluorescence or turbidity measurements. Such processes are carried out using sample supports or test strips made of transparent plastic and comprising a plurality of chambers or cup-shaped deepened portions formed with one open side. The sample supports or test strips comprise e.g. 32 or 96 chambers or deepened portions having a reagent arranged therein. After inoculation with a bacterial suspension, the sample supports or test strips are sealed by a transparent film or closed by a lid, if required. The deepened portions have a filling volume from 60 μl to 300 μl and are filled individually by means of auxiliary apparatus; pipettes having one channel or 8, 48 or 96 channels are used for this purpose.

From U.S. Pat. No. 4,038,151, a sample plate for an automated optical examination method is known, serving for the detection and counting of suspended microorganisms and for determining their sensitivity to antibiotics. The plate is made of rigid transparent plastic and comprises e.g. 20 conic reaction chambers. The cross-sectional area of the reaction chambers is larger on one side of the plate than on the other side. Provided next to each reaction chamber are two overflow chambers which are located on that side of each reaction chamber where an inflow channel for the respective reaction chamber is arranged. The reaction chambers are connected to overflow chambers via slits.

The reaction chambers, the slits and the overflow chambers extend over the complete thickness of the sample plate. The reaction chambers are connected in groups, via specially arranged and shaped inflow channels arranged on one plate side, to at least one sample receiving chamber closed by a septum. The inflow channels tangentially open out on the larger side of the conical reaction chamber. The form and the surface of the cross section of each inflow channel are formed with an abrupt change at a respective site. On these sides—when viewed in the flow direction—a flat and wide channel undergoes a transition into a deep and small channel. The inflow channels arranged on one plate side may be longer than the respective shortest connection between the reaction chamber and the sample receiving chamber so that a back diffusion of components arranged in the suspension will be rendered more difficult. The plate—except for an edge region—is on both sides bonded to a respective semipermeable film covering the reaction chambers, the overflow chambers, the slits, the inflow channels arranged on one side of the plate, as well as one side of the sample receiving chamber. The reaction chambers are covered by a dried layer of a reagent substance.

For introducing the sample liquid into the known sample plate, the channels and chambers of the sample plate are evacuated so that the sample liquid is passed from a container arranged externally of the plate via a cannula through the septum from the edge of the plate into the sample receiving chamber, and will flow via the inflow channels into the reaction chambers and, if required, into the overflow chambers.

The suspension (sample liquid) flown into the reaction chamber and the reagent layer are in contact with the adhesive layer arranged on the film.

During the optical examination of the samples in the reaction chambers, the sample plate is arranged vertically in the measuring device. In this orientation, the inflow channels, relative to the direction of gravity, are arranged to enter the reaction chamber from above, and the overflow chambers lie above the reaction chambers. Thus, gas bubbles which possibly exist in the reaction chamber or are generated in case of a reaction or a metabolic process, can accumulate in the overflow chambers without disturbing the optical examination of the samples.

From U.S. Pat. No. 5,670,375, a sample plate is known whose cavities, provided in a number of up to 64, are inoculated simultaneously. After the air has been sucked from the cavities, the fluid under examination will flow from a container arranged externally of the sample plate via a connecting tube into the cavities and thus will fill the latter.

Known from U.S. Pat. No. 5,223,219 is a sample support wherein, starting from a sample infeed region, sample liquid enters the reaction chambers via a distributor channel system. The reaction chambers contain porous inserts provided with reagents. By the capillary forces generated in the porous inserts, the sample liquid is "sucked" into the reaction chambers. The fact that the reaction chambers have inserts arranged therein, imposes restrictions on the photometric examinations of the sample liquids arranged in the reaction chambers and reacting with the reagents. Thus, for instance, this arrangement does not offer the possibility to perform transmitted-light measurements and optical-turbidity measurements.

Finally, the state of the art also includes liquid distributor systems for trans-porting a sample liquid from an ampoule into a plurality of reaction chambers wherein, in these systems, the force of gravity is utilized for generating a liquid flow through the distributor channels. The reaction chambers have to be vented, which is preformed by venting channels originating from the reaction chambers and by themselves forming a system of venting channels. Both of these channel systems (distributor channel system and venting channel system) are designed in the manner of communicating tubes, which—since gravity is utilized—prevents that the sample liquid might leak from the venting channels after the reaction chambers have been filled.

The increasing widening and automation of quasi-parallel examinations of microbiology and of analytical and diagnostic procedures require that the existing sample-support and sample-liquid distributor systems be further developed and particularly be miniaturized. Due to the thus resulting relatively small cross-sectional areas of the channels, it is desirable to use other forces than gravity and pressures for liquid transport. In this regard, particularly capillary forces would appear useful, which, however, would make it difficult to maintain the liquid transport even when the liquid is to flow from a region of a smaller cross section into a region of a larger cross section within the sample support and the sample liquid distributor system, respectively.

Thus, it is the object of the invention to provide a sample support and a sample liquid distributor system which have a relatively high density of reaction chambers per unit area, which can be produced at low costs and which include a liquid flow control mechanism controllable in a simple manner from outside.

According to the invention, the above object is achieved by providing a sample support and a sample liquid distributor system, respectively, comprising at least one sample receiving chamber for a sample liquid, a distributor channel for sample liquid, connected to said at least one sample receiving chamber, with at least one such distributor channel extending from each sample receiving chamber, at least one reaction chamber entered by an inflow channel branched off said at least one distributor channel, and a venting opening for each reaction chamber.

This inventive sample support and this inventive sample liquid distributor system is characterized in that each distributor channel and each inflow channel are dimensioned to have the liquid transport through the distributor and inflow channels effected by capillary forces, and that, in each reaction chamber, the entrance region of the inflow channel is provided with a means for generating a capillary force causing the sample liquid to flow from the inflow channel into the reaction chamber.

According to the invention, it is provided that the distributor channels and inflow channels have cross sectional areas of such small size and cross sectional areas of such shapes, respectively, that the liquid transport therein is performed by capillary forces. Thus, the channels are formed as capillaries. The reaction chambers provided to receive the sample liquid flowing via the channels, have a larger cross section than the inflow channels. In this manner, a situation is created where the liquid has to flow from a channel of a smaller cross section into a larger cavity, i.e. a reaction chamber. To have this flow performed exclusively under the effect of capillary forces, it is provided according to the invention that, in each reaction chamber, notably in the entrance region of the inflow channel, structures formed on the inner side of the reaction chamber or asymmetries are provided as means for generating a capillary force enabling a flow of the sample liquid from the inflow channel into the reaction chamber. By the provision of such capillary-force generating means in the entrance region of an inflow channel into a reaction chamber, the sample liquid flow generated by capillary forces is maintained until the reaction chamber has been filled. These capillary-force generating means enhance the wetting of the walls of the reaction chamber with sample liquid, thus maintaining the liquid flow constant. By way of alternative to the above mentioned designs of the capillary-force generating means, these can also be provided by surface treatment of the reaction chambers to the effect that these surfaces are made hydrophilic, or are made hydrophilic to such an extent that the interior sides of the reaction chambers are wetted and the reaction chambers are completely filled with sample liquid.

Particularly, the capillary-force generating means in the entrance region of the inflow channels into the reaction chambers are realized by the provision of an inflow groove or the like. This inflow groove comprises at least two limiting faces connected to each other by a transition region. This transition region is provided with rounded regions whose radii are small enough to generate the capillary forces required for the flow of the sample liquid along this groove. If the inflow channel is arranged to discharge into the reaction chamber at the height of the bottom face, then, by suitable selection of the rounding radius in the region between the bottom face and the side faces of the reaction chamber, the liquid flow can be maintained in that the liquid will first flow along the corner and transition regions between the bottom face and the side faces to thus wet the whole area, whereas, from that point, the further transport will be maintained by the capillary effect of the reaction chamber whose cross section is now completely filled with sample liquid. In a case where the inflow channel is arranged to enter the reaction chamber from above the bottom face out of one of the side faces of the reaction chamber, a groove or a similar furrow-like deepening should be formed in the respective side wall between the entrance and the bottom face. Such a groove can also suitably be provided by the corner region of two side faces of the reaction chamber extending to each other at an angle, provided that the rounding radius in the corner or transition region of both side faces is small enough to generate capillary forces acting on the sample liquid which are large enough to "pull" the sample liquid from the inflow channel. As to the required radii of curvature of these grooves, it should be generally observed that these are made smaller than the smallest dimension of the channel joined by the grooves.

By way of alternative to the capillary-force generating means, it can be provided that the channels extend under an angle other than 90° out from a face delimiting the chamber. Due to the resultant non-circular entrance opening, the sample liquid will in the most favorable case flow from the channel in to the chamber without additional measures.

The mechanism causing the sample liquid under examination to flow from the sample receiving chambers into the distributor channels, can likewise be obtained by use of structures generating capillary forces. In the simplest case, the distributor channels are arranged to branch off from the sample receiving chambers at the height of the bottom faces of the chambers. Since, after the filling of the sample receiving chambers with sample liquid, the cross section of the distributor channels are wetted with liquid in the entrance region, a flow within the distributor channels will be generated automatically. The discharge of the sample liquid from the sample receiving chambers is thus guaranteed.

A different situation exists if, usually for reasons of production technology, the distributor channels are arranged to enter the sample receiving chambers from above the bottom faces. In this case, it must be provided that the sample liquid is "pulled upward" starting from the liquid level within the sample chambers. This is effected by a capillary-force generating means, arranged in the sample receiving chamber, which can be configured in the same manner as the capillary-force generating means arranged in the reaction chambers. Also in this case, a preferred variant comprises a groove formed as an outflow groove in one of the side walls of the sample receiving chambers. As an alternative thereto, the groove can be provided as a transition region and corner region between two mutually angles side faces of the sample receiving chambers. In all of such cases, care must be taken that, by selecting a correspondingly small rounding radius of the groove and corner region, respectively, capillary forces are generated to cause the liquid to flow automatically.

As evident from the above description, miniaturization offers the possibility to arrange a large number of reaction chamber within an extremely small space, with the reaction chambers provided e.g. as cavities formed in a base body. As to the distribution of the sample liquid via the distributor channels and the inflow channels branching off therefrom, it is desirable that the sample liquid be caused to fill all of the reaction chambers in the most uniform manner possible and particularly simultaneously. To guarantee this effect—or largely guarantee it—in the distributor channel system provided according to the invention, the inflow channels should suitably have a smaller cross sectional area than the distributor channels. Thus, the inflow channels will act in the manner of throttles decelerating the liquid transport which is still generated by capillary forces. All of the inflow channels branching off along the length of the distributor channel can have the same cross sectional areas. Alternatively, the cross sectional areas of the inflow channels can be widened with increasing distance of the inflow channels from the sample receiving chamber, so that, in those inflow channels which branch off first—relative to the flow direction of the sample liquid through the distributor channels—a larger throttle effect is obtained than in the inflow channels branching off later.

For reasons of space, the inflow channels are suitably arranged to branch off from the distributor channels on both sides thereof. In this regard, under the aspect of flow technology, two branch-off sites of the distributor channel which have mutually opposite inflow channels branching off therefrom on opposite sides, should advantageously not be arranged directly opposite each other but at a mutual displacement along the length of the distributor channel. Notably, each inflow channel branching off from the distributor channel will disturb, although just slightly so, the liquid transport maintained by the capillary forces. For these reasons, such disturbances should not at the same time affect the liquid front moving along the distributor channels, which would be the case if two mutually opposite, branched-off inflow channels were to branch off at the same height of the distributor channel and/or directly opposite each other.

To make it possible that sample liquid can flow into the reaction chambers from the sample receiving chambers, it must be provided that the gas contained in these chambers and in the channel system leading thereto is allowed to escape. For this reason, each reaction chamber is provided with a venting opening. If these venting openings are wetted or even covered while the reaction chambers are being filled with sample liquid, a danger exists that the sample liquid escapes from the reaction chambers via the discharge openings if the wetting and covering of the venting openings can cause large enough capillary forces therein. In fact, it is desirable that the reaction chambers be completely filled with sample liquid because any gas which might still have entered would make the optical examination by photometry more difficult or even impossible.

Advantageously, further transport of the sample liquid through the venting openings is prohibited by use of means preventing further flow of sample liquid. Such means are advantageously based on the principle of utilizing geometric shapes of the venting openings and of possibly joining venting channels to make the generated capillary forces small enough to cause an interruption of the sample liquid flow. To be particularly preferred in this regard are so-called "capillary jumps", i.e. enlargements of the channels into which the sample liquid cannot flow by because of more-difficult wetting conditions on the walls of the widened channel portions. For instance, venting channels joining the venting openings can be arranged to enter a cavity and a widened portion of the channel, wherein the entrance region is arranged within a side surface of the widened channel portion or cavity and no or few corner regions are arranged around the entrance region. This is provided because each corner region would again generate capillary forces which in turn are determined by the extent of the rounding.

Suitably, the venting openings of the reaction chambers are followed by connection channels entering a venting collecting channel. This venting collecting channel is provided with a venting opening which connects the venting system of the sample support with the environment. Since there is thus provided a second distributor channel system which from a central site, i.e. the venting collecting channels, allows for a fluid connection to the individual reaction chambers, it is desirable to utilize this second distributor system for a well-aimed introducing of additional reagent liquids into the reaction chambers. By introducing additional reagent liquids, the sample liquids which in the reagent chambers have already undergone a reaction with a reagent sub-stance that had been introduced thereinto in advance and arranged therein e.g. in dried form, can be subjected to a second reaction. Since, however, the venting system is already provided with a means, particularly in the form of widened channel portions, which is to prevent a liquid flow from the reaction channel portions, which is to prevent a liquid flow from the reaction chambers via the venting openings, such means will also impede the transport of the reactive liquid via the venting channel system into the reaction chambers. In this regard, it is of advantage if, by a corresponding configuration of the widened channel portions forming the flow prevention means, it is safeguarded that the flow of reagent liquid into the widened channel portions under the effect of capillary forces is taking place. In this regard, use can be made again of the inflow groove structures described already further above which can be realized by correspondingly designed corner regions in the transition region of a plurality of mutually angled faces of the widened channel portions.

By providing the widened channel portions with capillary force generating means allowing the inflow of reagent liquid into the widened channel portions, the latter are filled with reagent liquid until the reagent liquid covers the entrance region of the portions of the venting channels from the reaction chambers. Thus, in this entrance regions, the two reagent liquid and sample liquid fronts will contact each other. The further transport of the reagents will now be performed by diffusion up into the reaction chambers.

The well-aimed filling of the widened channel portions for effecting the diffusion transport of the reagents, can alternatively be obtained also by introducing a control liquid (which is inert toward the reagents and the sample liquids). For this purpose, a control channel is arranged to enter the widened channel portion, with the control liquid reaching the widened channel portion via this control channel. In this manner, a liquid-controlling valve is provided, which, as it were, allows for a single actuation for switching the valve from the closed condition into the open condition with regard to the possibility of a diffusion transport of the reagents. The introducing of the control liquid into the widened channel portions can be carried out by application of pressure or again by use of capillary forces. For this purpose, use can be made again of the same mechanisms and designs of the side wails and entrance regions that have been described further above.

The introducing of the reagent liquid into the venting collecting channel and the venting channel system, respectively, of the reaction chambers is suitably performed in that this channel system is in fluid connection with at least one reagent liquid receiving chamber. From this chamber, the reactive liquid will be discharged particularly by use of those mechanisms described further above in connection with the sample receiving chambers and the distributor channels.

For the examination of microbiological samples using the inventive sample support, it may be required that the sample under examination be amplified beforehand, i.e. that the quantity of the sample material be increased before the material is fed to the individual reaction chambers via the distributor inflow channel system. The process of the amplifying and of the introducing the amplified sample into sample receiving chambers is simplified if the amplification itself is performed at the site of the sample receiving chamber. In this case, it is desirable that the amplified sample material is supplied, under external control, to the reaction chambers assigned to the sample receiving chambers. According to an advantageous variant of the invention, this is performed in that, between the sample receiving chamber and the first inflow channel branching off the at least one connecting channel, a first valve is arranged which is preferably arranged as a one-way valve which can be switched from its closed condition into its open condition only once. If the transport of the sample from the sample receiving chamber to the individual reaction chambers is performed by capillary forces—which is to be preferred, and which is why all of the channels in the sample support are formed as capillaries—then this first valve can also be arranged in the venting channel which is associated with a group of reaction chambers connected to the sample receiving chamber. Notably, by the thus obtained controlled venting of the reaction chambers, the inflow of the sample material from the sample receiving chamber to the individual reaction chambers will be controlled.

The "interface" of the inventive sample support for driving the first valve or the first valves should be of the simplest possible configuration. This necessitates that the valve can be controlled in a simple manner from an external site. Preferably, it is provided that the valve be controlled hydraulically or pneumatically, notably by the liquid and respectively the gas on this valve. Particularly, for instance, by applying a pressure pulse on the sample material contained in the sample receiving chamber, a hydraulic pressure is generated on the first valve which will overcome or otherwise bridge the locking element of the first valve. Thus, for instance, it is possible to design the first valve as a burst valve comprising a burst film designed to burst open when a specific pressure is exceeded, thus opening the channel in which the valve is arranged. By way of alternative, flap valves or back-check valves can be used which will open when a corresponding pressure of the applied fluid (liquid or gas) is reached. This type of valves is preferable particularly if the transport of the fluids through the sample support is performed by application of pressure, i.e. not through capillary forces.

A further alternative of the design of the first valve or the first valves resides in that this valve is of a hydrophobic design which is realized by a corresponding surface treatment of the channel in the region of the valve or by an insert portion. The fluid applied to the hydrophobic valve will bridge the valve e.g. as a result of a—particularly pulse-like—application of pressure. When the channel in the region of the valves is in this manner wetted with liquid and use is made of capillary forces for the further transport of the liquid, these provisions will generate a one-way valve which can be externally bridged in a simple manner, i.e. by applying pressure onto the sample receiving chamber. Further, the first valve can advantageously provided as a widened portion of the channel, which in turn will act as a capillary jump. (In this regard, cf. the description in connection with the venting channels further above.) As soon as this widened channel portion has been filled with liquid, which is performed e.g. by corresponding application of pressure to the sample receiving chamber or externally by introducing a separate or control liquid, the transport of the liquid behind the valve, caused by capillary forces, will be safeguarded so that the valve itself can be bridged again hydraulically.

All of the channels, chambers and the like structures are placed, preferably from one side, in a base body covered in a liquid-tight manner by a lid body, particularly a film. Alternatively, both bodies, the base body and the lid body, can together form the channels and cavities. The sample support is preferably made of plastic, such as polystyrene or polymethyleneacrylate (PMMA), polycarbonate or ABS. The sample support can be produced by casting respectively one shaped insert in a micro-injection mold. In this case, the structure of the shaped insert is complementary to the structure of the base body and/or the lid body. The shaped inserts to be used for these injection molding techniques are produced by lithography or galvanoplasty, by microerosion or by micromechanic treatment such as diamond machining. Further, the structured elements of the sample support can be produced from a photo-etchable glass or from silicon by anisotropic etching or by micromechanic treatment processes. The components of the sample support (base boy and lid body) are connected to each other on their contacting faces, particularly by ultrasonic welding. In any case, this connection must be liquid- and gas-tight so that the individual chambers and channels will not be in mutual contact via contacting faces of the elements from which the sample support (base body and lid body) is made.

The inventive sample support can comprise transparent material for use in transmitted light measurements, and transparent or non-transparent material for luminescence measurements. If the sample support is made from several components (base body and lid body), the individual components of the sample support can comprise different materials.

The height of the reaction chambers and thus the thickness of the liquid layer having the light passing therethrough can be adapted to the optical evaluation method. Within the sample support, reaction chambers with different heights can be arranged.

The inventive sample support can comprise reaction chambers with volumes in the range from 0.01 μl to 10 μl. The density of the reaction chambers can be up to 35/cm$^2$. Thus, one sample support of a handy size can easily accommodate 50 to 10,000 reaction chambers. The individual channels have a width and depth of 10 μm to 1,000 μm and particularly 10 μm to 500 μm.

A sample support configured according to the invention has a height of e.g. 4 mm, wherein, for a two-part configuration (base body and lid body), the base body has a thickness of about 3.5 m and the lid body, provided as a film, has be thickness of 0.5 mm. The reaction chambers, which—if desired—are round but may also be edgy, have a depth of about 3.0 mm so that the bottom wall will have a thickness of 0.5 mm. The volume of these reaction chambers is respectively 1.5 μl. The individual channels particularly have a rectangular cross section, wherein the inflow channels have a width of about 400 μm and a depth of 380 μm, and the distributor channels having the inflow channels branching off therefrom have a width of about 500 μm and a depth of about 380 μm. The venting openings (in case of a rectangular cross section) are about 420 μm wide and about 380 μm deep. The venting channels joining the venting openings particularly have a width and depth of 500 μm and 1,000 μm, respectively. A surface of 21.5 mm×25 mm, i.e. of 540 mm$^2$, has arranged thereon 96 reaction chambers suited to be filled simultaneously. Thus, under the arithmetic aspect, the area required by the reaction chamber is 5.6 mm$^2$.

The inventive sample support particularly has the following advantages:

- The sample support contains a substantially larger number of reaction chambers with smaller volumes, resulting in a larger density of the sample cambers.
- Filling the reaction chambers with the sample liquid is performed faster and
- while requiring lesser apparatus components—in a simpler manner, since the sample liquid will be applied only at a few sites (sample receiving chambers) and will automatically flow from there into the reaction chambers under the effect of capillary forces.
- Filling the reaction chambers requires neither an overpressure of the sample liquid nor an underpressure in the reaction chambers.

- The sample receiving chambers are filled by use of devices of commercially available types, with the sizes and volumes of the sample receiving chambers being adapted to such devices.
- In a sample support provided with sample receiving chambers for the reagent liquid, a reagent liquid existing in a liquid can be easily introduced at a later time into the reaction chambers already filled with a fluid.
- The sample material can be introduced in a well-aimed manner from the sample receiving chamber into the individual reaction chambers, notably by provision of a first valve in the channel system completely joining the sample receiving chamber.
- Also the reagent liquid, which—if desired—is fed into the reaction chambers from their venting side, can be introduced into the reaction chambers in a controlled manner due to the provision of second valves in the venting duct. These second valves can be controlled particularly hydraulically, pneumatically and in similar manners, as is the case for the first valves.
- The covered reaction chambers are completely filled with the fluid under examination. The filing volume of each reaction chambers is determined automatically; a dosage mean for each individual reaction chamber is not required.
- During a possible further treatment and during measurement, the fluid contained in the reaction chambers is effectively protected from evaporation by the cover film tightly connected to the base body.
- The material required for introducing a reagent into the reaction chambers, the required testing material, e.g. blood suspension, blood samples or active substances, and thus the costs, are less than in sample supports with reaction chambers having larger volumes.
- For the fluid under examination, e.g. a bacterial suspension, sample receiving chambers can be provided which are arranged in the base body or in the lid body and which, if desired, have a plurality of connecting channels entering thereinto.
- The microbiological, microchemical or bacteriological examination of the samples introduced into the sample support can be fully automated while the expenditure for the measuring devices is reduced.
- The sample support can be stored at normal room temperature. The space requirement for storage is distinctly less than in conventional sample supports.
- The sample supports, in analogy with known sample supports, are designed for single use. Because of the enlarged packing density of the reaction chambers, the volume of used sample supports to be disposed of is smaller than when using conventional sample supports.

By use of an adapted miniaturized device, the reaction chambers in the sample support can be provided with a chemically or biologically active reagent which after the introducing of the reagent fluid will be dried and adhere on the bottom and the wall of the reaction chambers. Useful as reagents are e.g. oligopeptide-β-NA-derivates, p-nitrophenyle-derivates, sugar for fermentation examinations and other examinations, organic acids, amino-acids for assimilation examinations, decarboxylase substrates, antibiotics, antimycotics, nutrient substrates, marker substances, indicator substances and other substances.

The inventive sample support which to be provided with a reagent, if required, can be used for the biochemical detection and the sensitivity testing for clinically relevant microorganisms. In a fully automated and miniaturized system. there is produced a defined suspension of microorganisms which is delivered to the sample support. The inoculated sample support is—possibly after a further treatment—measured by use of an optical method. The results obtained thereby are picked up under the assistance of a computer and are mathematically examined and evaluated through suitably adapted methods.

The inventive sample support is useful in blood-group serology, in clinical chemistry, in the microbiological detection of microorganisms, in testing the sensitivity of microorganisms to antibiotics, in microanalysis and in the testing of production materials.

BRIEF DESCRIPTION OF THE DRAWINGS

The invention will be explained in greater detail with reference to the Figures.

Figure 5:
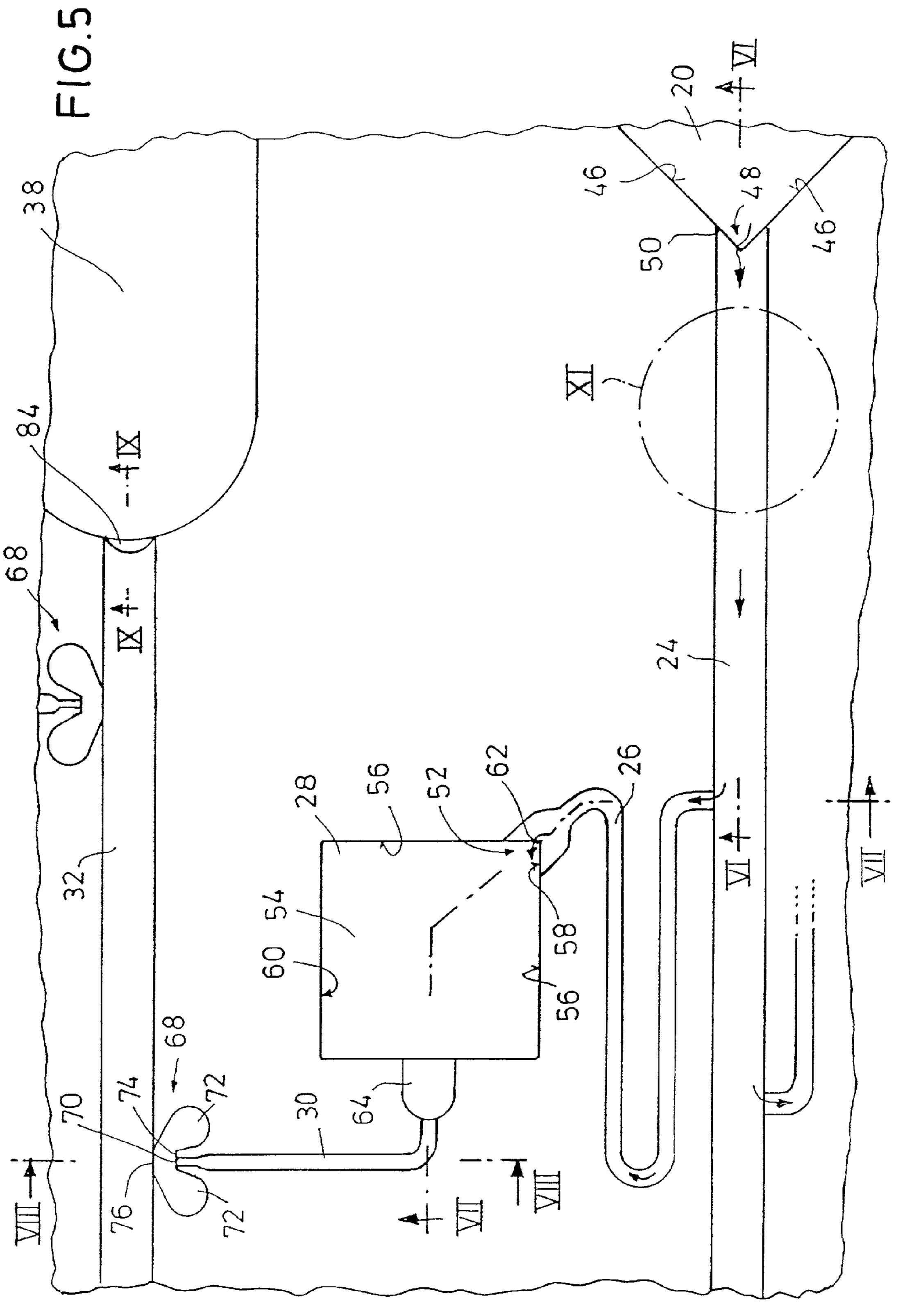
FIG. 5 is a view of the area of the sample support marked by V in FIG. 1, in perspective view and enlarged representation.

FIGS. 10 to 14 are views of different valve configurations in plan and sectional views, with the valves arranged in the region marked by XI in FIG. 5.

Figure 1:
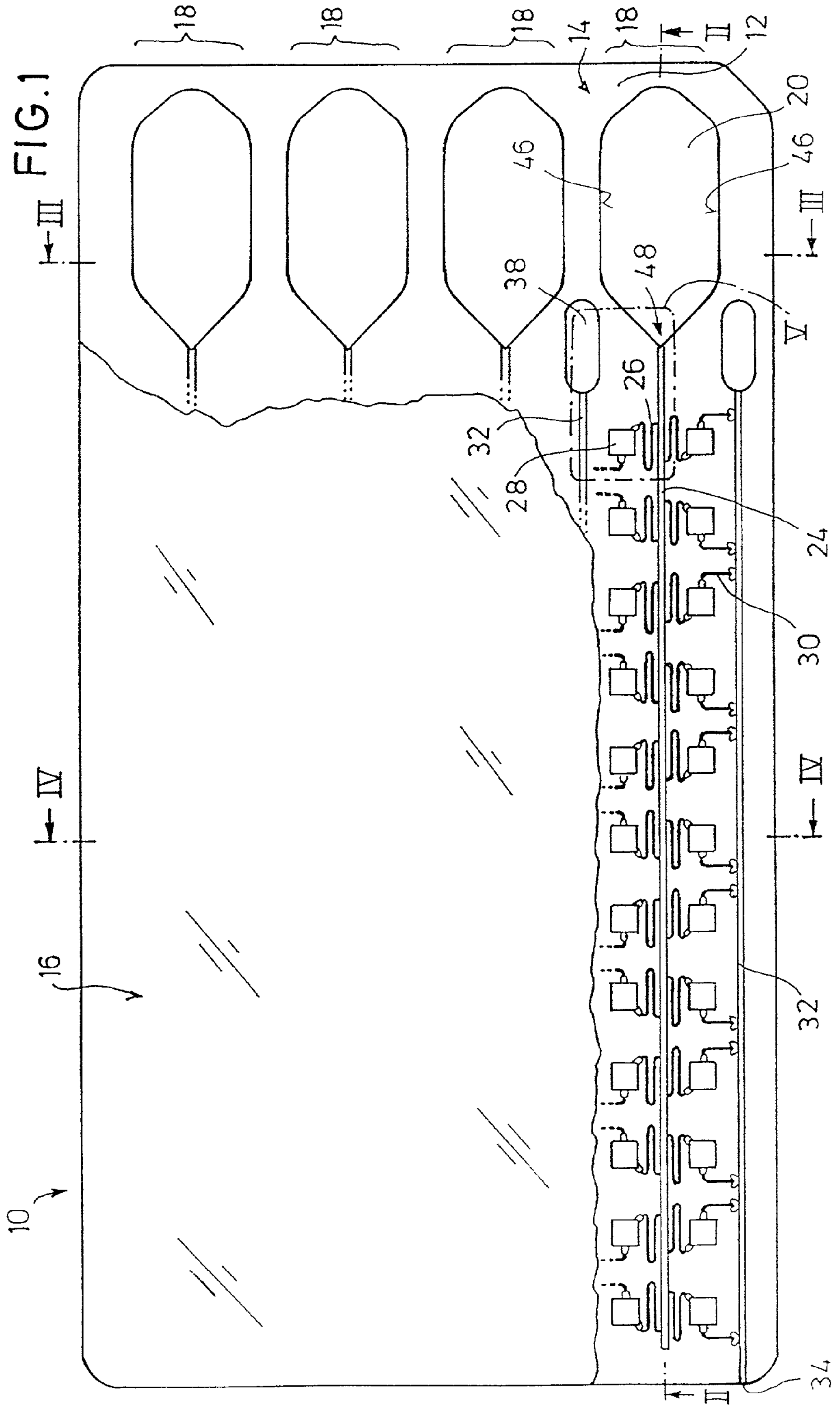
FIG. 1 is a plan view of the upper side of a sample support, with the cover film partially broken away.
Figure 2:
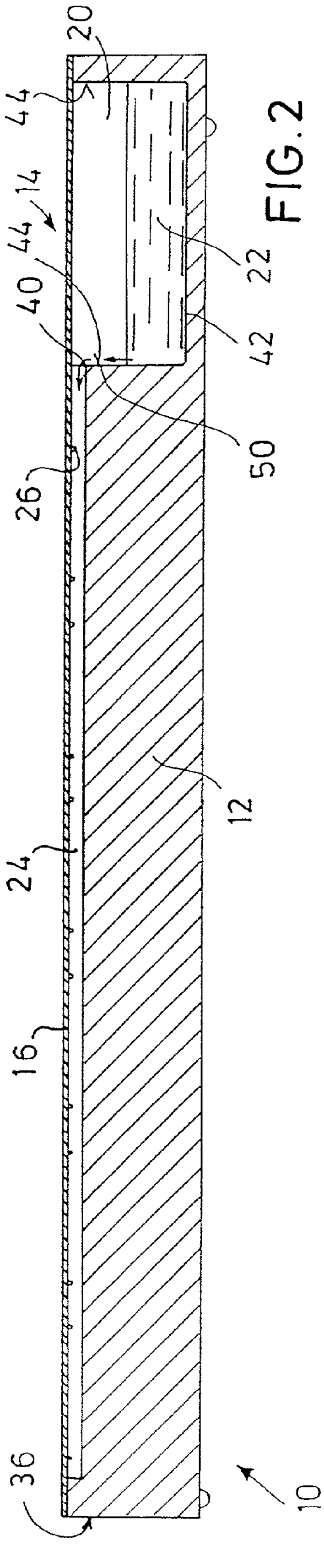
FIG. 2 is a sectional view, taken along the line II-II in FIG. 1, of a sample receiving chamber with a distributor channel joining the same.
Figure 3:
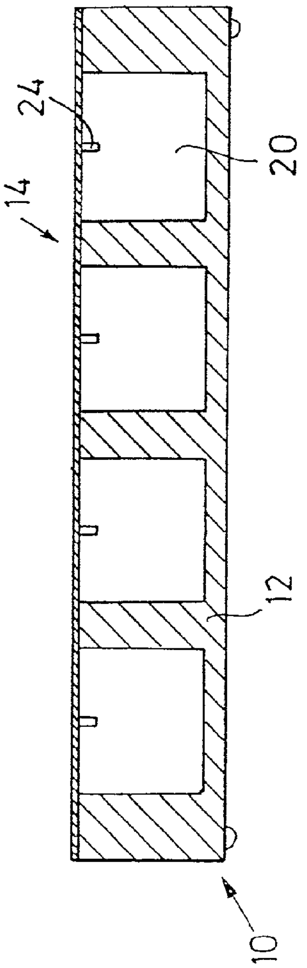
FIG. 3 is a sectional view, taken along the line III-III, of the sample chambers, showing also the distributor channels branching off therefrom.
Figure 4:
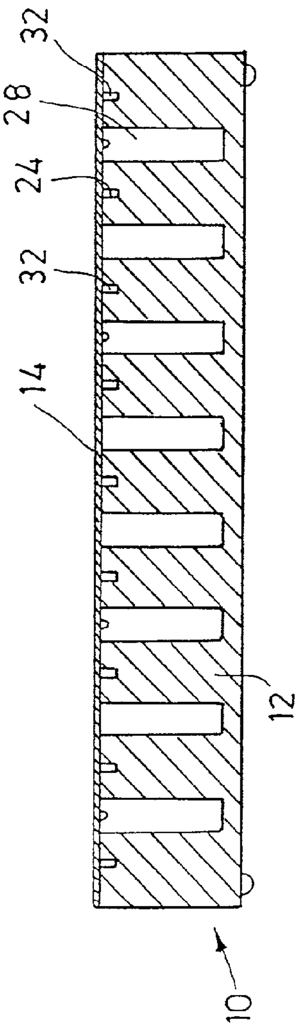
FIG. 4 is a sectional view, taken along the line IV-IV in FIG. 1, of the reaction chambers arranged adjacent each other along the width of the sample support.

The sample support 10 illustrated in the drawing is of a two-part structure and comprises a base plate 12 whose upper side 14, shown in FIG. 1, is covered by a cover film 16 (cf. also FIGS. 2 to 4). Sample support 10 is provided to direct applied sample liquid into a plurality of reaction chambers under the effect of gravity, with the reaction chambers having different reagent substances arranged therein. Further, it is required that the reaction chambers filled with sample liquid can be photometrically examined. Further, it is provided that liquid can be inserted into the reaction chambers in a controlled manner from different sites.

As particularly evident from FIG. 1, sample support 10 is divided into a plurality of sections 18 of mutually identical configurations. In the subsequent description, reference is made each time to the configuration of one such section. Within each section 18, the base plate 12 of sample support 10 is provided with a structured surface on its upper side 14, which is realized by forming grooves and deepened portions into the base plate 12 from upper side 14. All of the grooves and deepened portions constitue a sample-liquid and reagent-liquid distributor system which towards the upper side of sample support 10 is covered by cover film 16.

Each section 18 of sample support 10 includes a sample receiving chamber 20 for receiving a sample liquid 22 (cf. FIG. 2). Arranged in fluid connection with the sample receiving chamber 20 is a distributor channel 24 entering the sample receiving chamber 20 on the upper end of the chamber. Inflow channels 26 extend from distributor channel 24 on both sides thereof and in a serpentine configuration when seen in plan view according to FIG. 1, which channels like the distributor channel 24 are generated by the formation of grooves in the upper side 14 of base plate 12. The inflow channels 26 extend from distributor channel 24 to the reaction chambers 28 which are arranged as deepened portion formed in base plate 12 from upper side 14. Connecting (venting) channels 30 extend from the reaction chambers 28. These connecting channels 30 are arranged to enter group-wise into two venting collecting channels 32 extending in parallel to each other and in parallel to the distributor channel 24. In other words, the reaction chambers 28 arranged on both sides of distributor channel 24 extend between distributor channel 24 on the one hand and one of the two venting collecting channels 32 on the other hand. Also the connecting channels 30 and the venting collecting channels 32 are generated by the formation of grooves in the upper side 14 of base plate 12. Further, the venting collecting channels 32 have their upper ends terminating in a venting opening 34 formed in an outer edge side 36 (cf. FIG. 2) of base plate 12. The respective end of the venting collecting channels 32 which is arranged opposite these venting openings 34, is connected to a reagent liquid receiving chamber 38 to be discussed later. Also this chamber 38 is realized by forming a deepened portion in the upper side 14 of base plate 12.

The transport of sample liquid 22 from a sample receiving chamber 20 of a section 18 of sample support 10 into the reaction chambers 28 assigned to sample receiving chamber 20 is performed by use of capillary forces. The same applies to the transport of reagent liquid from chambers 38 into reaction chambers 28. To make it possible that these capillary forces are generated within the channels, these channels 24,26,30,32 have to be dimensioned in a suitable manner. If required, the inner sides of the channels have to be subjected to a surface treatment to render these surfaces hydrophilic. Whether such a treatment is required, will depend on the material of base plate 12 and cover film 16 on the one hand, and on the viscosity and the nature of the to-be-transported liquids (sample liquid and reagent liquid) on the other hand.

While the utilization of the capillary forces within the channels can be realized in a simple manner by the above described measures, achieving a reliable transport of liquid from the chambers 20,38,28 into the connected channels and respectively out from the channels 26 into the connected reaction chambers 28, is problematic. With regard to the fluid connection of distributor channel 24 to the sample receiving chamber 20, a problem resides particularly in that the entrance site 40 of distributor channel 24 into sample receiving chamber 20 is located above the bottom wall 42 of chamber 20 and within the lateral delimitation 44 of chamber 20. The lateral delimitation 44 of chamber 20 is formed by side face portions 46. As can be seen particularly in FIG. 1, the side faces 46 extend in angular orientations in the region below the entrance site 40, in this case under a mutual angle of about 90°, so that a corner region 48 is generated between both side faces 46. This corner region 48 has such a small radius of curvature on its bottom that there is formed an outflow groove 50 in which a liquid meniscus is generated upon wetting with sample liquid 22. In the instant case, this outflow groove 50 extends transverse to bottom wall 42. Thus, as a result of the wetting of the side faces 46 in the corner region 48, capillary forces are generated in the outflow groove 50, which forces are sufficient to act on the sample liquid 20 to the effect that the sample liquid 22 is sucked from sample receiving chamber 20 into distributor channel 24. The outflow groove 50 extends particularly all the way to the bottom wall 42 of sample receiving chamber 20. As soon as the cross sectional area of distributor channel 24 is completely filled by the sample liquid 22, the further trans-port of the sample liquid in distributor channel 24 is performed by capillary forces which are effective within the channel.

The inflow channels 26 are arranged to branch off from distributor channel 24 transversely to the extension thereof. Also in these inflow channels 26, the further transport of the sample liquid 22 is performed by capillary forces. The liquid transport through the inflow channels 26 will extend first to the entrance site 52 of each inflow channel 26 into the reaction chamber 28 assigned to the channel (cf. FIG. 5). Without taking special measures or observing special conditions with regard to the configuration of the inflow channels 26 and the reaction chambers 28, a danger exists that the liquid front will not extend farther into the reaction chamber 28 from the entrance site 52 of the inflow channel 26.

To further guarantee a reliable liquid transport by capillary effect in the above situation, the entrance site 52 is arranged on the upper end, facing away from the bottom wall 54 of a reaction chamber 28, of two mutually angled side faces 56 of reaction chamber 28. The overall reaction chamber 28 is of a square or at least rectangular cross section (cf. the illustration in FIGS. 1 and 5) so that corner regions 58 and 60, respectively, are generated between respectively adjacent side faces 56 and between the side faces 56 and the bottom face 54. By forming these corner regions with a sufficiently small radius of curvature, a liquid meniscus can be generated in the transition region of the faces forming the respective corner regions, which meniscus—due to the tendency of the liquid to wet the adjacent regions of the faces—will be moved along the corner regions 58,60 under the effect of capillary forces.

Thus, the corner region 58 having the entrance region 52 of the inflow channel 26 arranged therein, acts as an inflow groove 62. This inflow groove 62 allows a flow of the sample liquid 22 from the inflow channel 26 into reaction chamber 28. This liquid first flows along the inflow groove 62 in the direction towards the bottom face 54 of reaction chamber 28, and flow from there along the corner regions 58 which extend continuously in the shape of a square, until the whole bottom of reaction chamber 28 is wetted. In this manner, the reaction chamber 28 is increasingly filled with sample liquid exclusively by use of capillary forces.

The filling of the plurality of reaction chambers 28 should be performed in a uniform manner and particularly simultaneously. A too sudden filling of the reaction chambers 28 with sample liquid 22 can lead to undesirable effects because the sample liquid 22 might possibly flow off again undesirably via the connecting channels 30 provided for venting. Therefore, it is advantage to have the sample liquid 22 admitted into the reaction chambers 28 in throttled fashion. For this reason, the cross sections of the inflow channels 26 are smaller than the cross section of the distributor channel 24. The inflow channels thus form a kind of throttle with increased flow resistance. This throttle effect offers the additional advantage that, although the individual inflow channels branch off from the distributor channel 24 at different distances from the sample receiving chamber 20, all of the reaction chambers 28 are filled simultaneously (with a certain delay being tolerated).

As can be seen particularly in FIGS. 1 and 5, the inflow channels 28, when viewed along the extension of distributor channel 24, are arranged to branch off therefrom in a mutually staggered relationship. This has the advantage that the liquid front advancing through the distributor channel 24 is respectively "disturbed"—in the region where the inflow channels 26 branch off—only by the entrance opening of an inflow channel 26. Notably, if the inflow channels 26, arranged in pairs on both sides of distributor channel 24, were to branch off opposite to each other, the liquid transport could be disturbed to an extent which would cause it to stop. In this regard, it is to be considered that an unevenness of the surface can sometimes massively impair the effective capillary forces. The branching of an inflow channel 26 from the distributor channel 24 acts like a widening of the channel which, if too large, could bring the flow to a standstill. Notably, the transport through a branched-off inflow channel 26 by capillary forces acting therein will occur only when the liquid in distributor channel 24 covers the cross section of the branched-off inflow channel 26. For this reason, the inflow channels 26 have cross sections small enough that they will ultimately pose no obstacle to the tendency of the liquid to wet the inner walls of distributor channel 24 in spite of the branched-off inflow channel 26.

Figure 7:
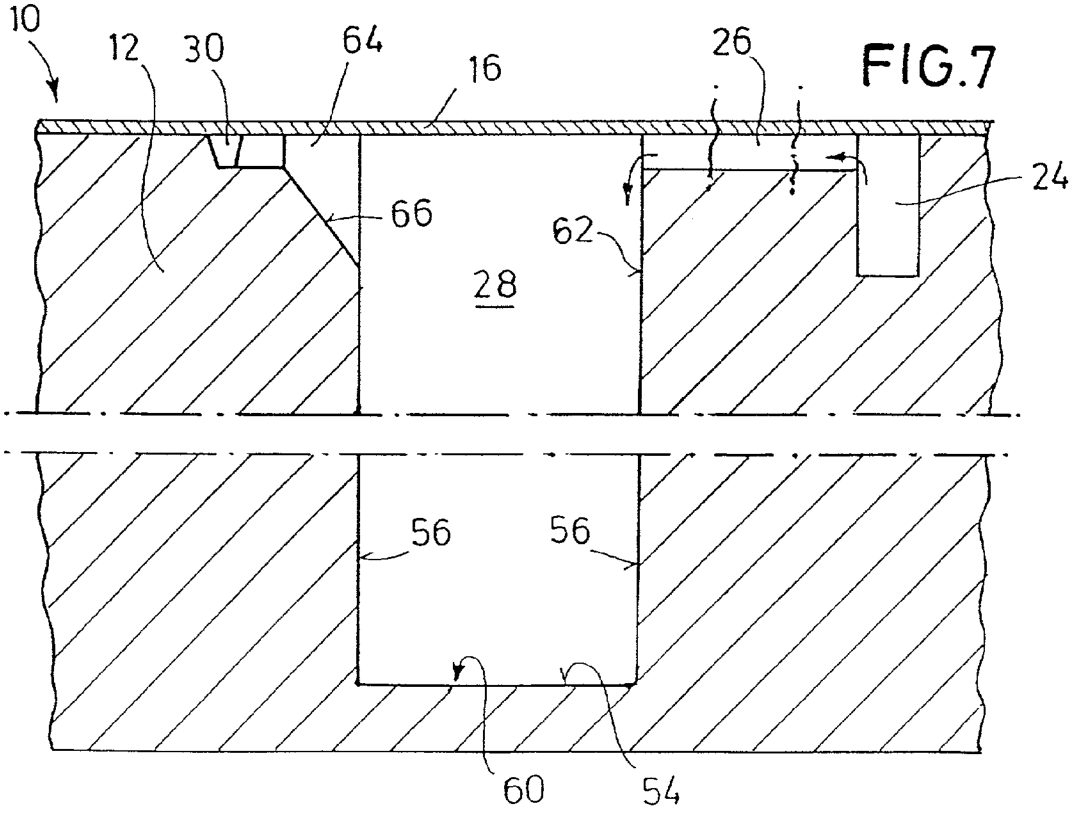

During the filling of the reaction chambers 28 with the sample liquid 22, air or gas existing within these chambers is discharged via the connecting channels 30. Each connecting channel 30 is arranged to enter the respective reaction chambers 28 via an antechamber space 64 (cf. also FIG. 7). Antechamber space 64 is arranged on the upper end of reaction chamber 28 and delimited in upward direction by cover film 16. The bottom wall 66 of antechamber space 64 opposite cover film 16 extends obliquely downwards in the direction of reaction chamber 28. The configuration of antechamber space 64 is selected such that all of the air or gas in reaction chamber 28 will be discharged when the latter is being filled so that, finally, the liquid level within reaction chambers 28 will reach up to cover film 16 and will not be disturbed by gas bubbles and the like. As is evident particularly from FIG. 5, the connecting channels 30 serving for the venting of the reaction chambers 28 are arranged to enter the venting collecting channel 32 via widened portions 68 which are heart-shaped when seen in plan view. Each widened portion 68 comprises chamber portions 72 extending on both sides of the entrance 70 of connecting channel 30 and reaching to a region—relative to the gas flow direction—upstream of the entrance site 70 and tapering towards the venting collecting channel 32. The entrance side 70 is located in a side face region 74 of the widened portion 68, with the side face region 74 having no corner regions arranged therein, neither laterally of nor below the entrance site 70. The only corner region existing is generated laterally of the entrance site 70 and adjacent to film 16. Thus, the connecting channel 30 ends within the widened portion 68 in such a manner that its entrance site 70 is surrounded by areal portions. An entrance site 70 of this type has the advantage that the oncoming liquid front is stopped at the entrance site 70 because a further transport thereof is prevented by capillary forces. This liquid front will move on through the connecting channels 30 since, after the complete filling of the reaction chambers 28, the sample liquid will move, via antechamber space 64, into the connecting channels 30 acting again as capillaries. Thus, the widened portion 38 prevents that the sample liquid proceeds into the venting collecting channel 32.

As mentioned already above, each venting collecting channel 32 extends from a reagent liquid receiving chamber 38. Contained in these receiving chambers 38 is an additional reagent liquid which is required to initiate reactions of the sample liquid in the reaction chambers 28. The reaction chambers 28 are advantageously provided beforehand with reagent substances which have been preconditioned and introduced into the reaction chambers 28 according to the examinations to be performed. Until the inflow of the sample liquid 22, these reactive substances are arranged in dried form within the reaction chambers 28.

When the reaction of the sample liquid with the reactive substances already contained in the reaction chambers 28 has been completed, it may be required to induce an additional reaction. For this purpose, the conduit system which comprises the venting collecting conduits 32 and the connecting conduits 30 as well as the widened portions 68 and up to then has been used as a venting system, is thereafter utilized for introducing additional reagents into the reaction chambers 28. For this use, it should be safeguarded that the widened portions 69 can be passed by the reagent liquid. This can be realized, for instance, by configuring the entrance sites 76 of the venting collecting channels 32 into the widened portions 68 in such a manner that the inflow of the reagent liquid into the widened portions under the effect of capillary forces will be guaranteed. Useful for this purpose are the same mechanisms that have been described farther above in connection with the inflow of the sample liquid 22 from the inflow channels 26 into the reaction chambers 28. By the formation of corner regions with sufficiently small rounding radii in the immediate vicinity of entrance site 76, the inflow of reagent liquid into the chambers 72 of the widened portions 68 through capillary forces can be obtained. As a further alternative, it can be provided that the application of an hydraulic pressure onto the reactive liquid in the chambers 38 causes the widened portions 68 to be filled with reactive liquid. A third possibility consists in a controlled introducing of a control liquid into the widened portions 68. (The control channels and control liquid receiving chambers required therefore are not illustrated in the Figures.) All of the variants described here have in common that the further transport of the reagent substances in the reagent liquid into the reaction chambers 28 requires that the widened portions 68 be filled with liquid. As soon as these portions 68 have been filled with liquid, this liquid will at the entrance site 70 contact the sample liquid arranged in the connecting channel 30. The further transport of the reagents of the reagent liquid is then performed by diffusion. In other words, the widened portion 68 forms a bi-directional valve which, depending on the flow direction, is either in the closed condition or in the open condition.

Figure 6:
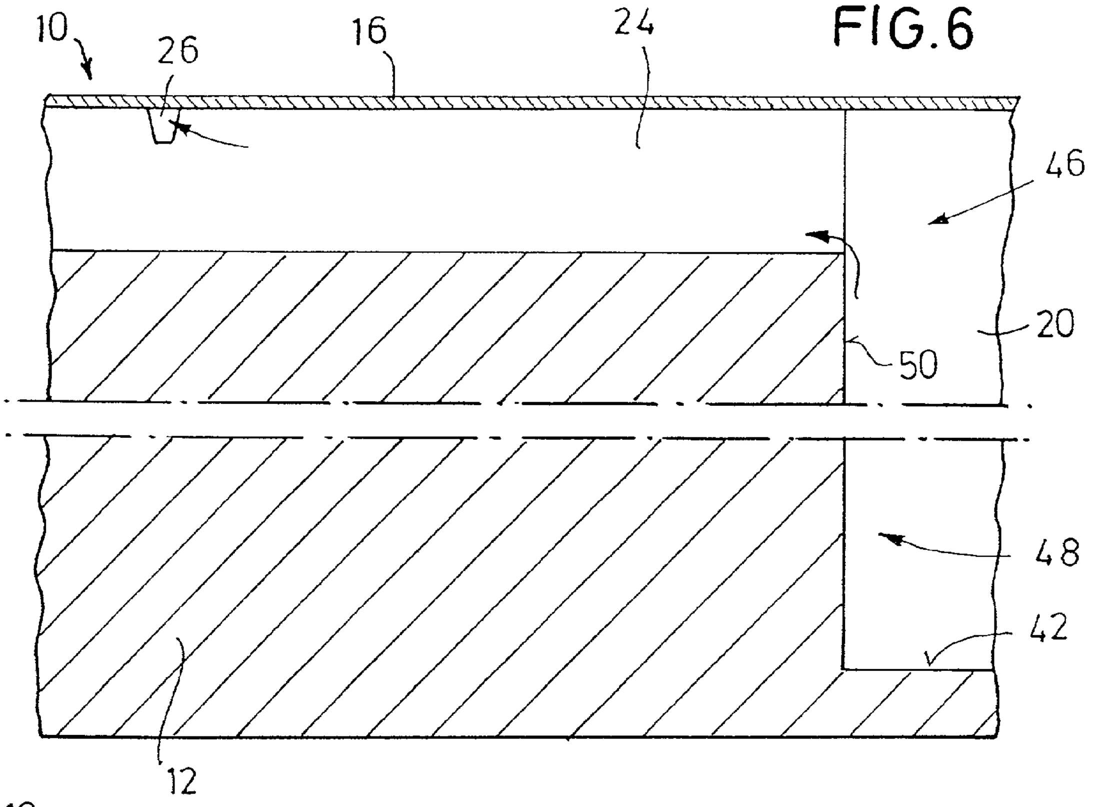
FIGS. 6 to 9 are cross-sectional views, taken along the lines VI-VI through IX-IX in FIG. 5, illustrative of the configuration of the channels and chambers respectively in their transition regions and entrance regions.
Figure 9:
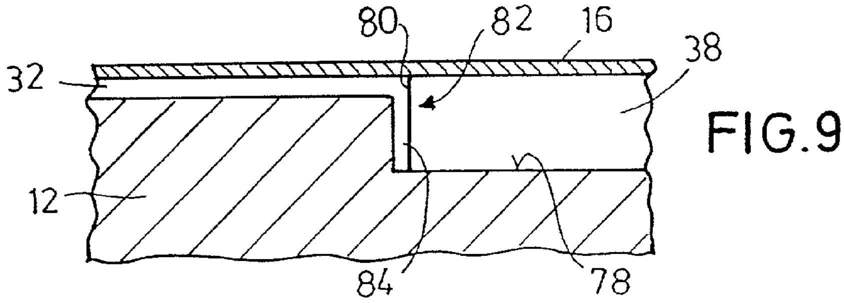

For the sake of completeness, it should be pointed out with reference to FIGS. 5 and 9, that also in this case, use is made of capillary forces for transport of the reagent liquid from the reagent receiving chambers 38 into the venting collecting channels 32 joining the latter. This mechanism is similar to the one described in connection with FIGS. 1 and 6. According to FIG. 9, the venting collecting channel 32 is arranged to branch off at the upper end facing away from the bottom wall 78 of chamber 38. In this region, the entrance site 80 in the side wall delimiting region 82 of chamber 38 is rounded as shown in FIG. 5. To realize a flow, based on capillary forces, out of chamber 38 into channel 32, there is again required a sort of outflow groove 84 with a radius of curvature small enough to generate a liquid meniscus which, due to the tendency of the liquid to wet the groove 84, will move along this groove, in this case in the upward direction.

With reference to FIGS. 10 to 14, constructional possibilities of valve configurations will be discussed hereunder which make it possible to have the liquid from the sample receiving chambers flow into the connected distributor channels 24 in a controlled manner.

Figure 10:
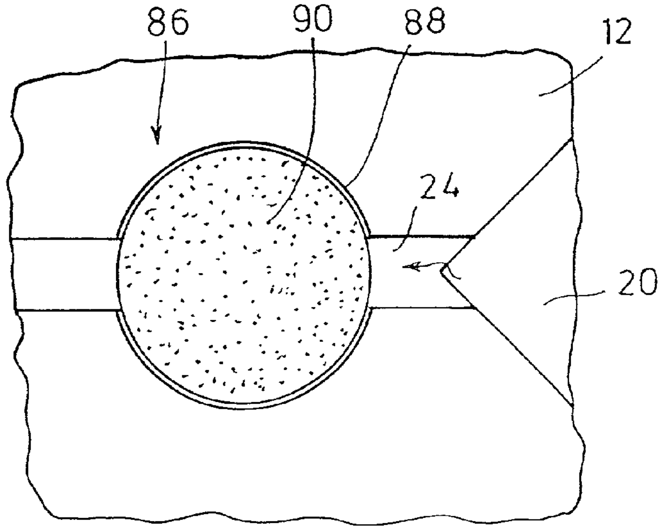

A first variant of such a valve 86 is shown in FIG. 10. In this valve construction 86, the distributor channel 24 extends through a widened channel portion 88 which is round in plan view and has a porous hydrophobic insert body 90 arranged therein. Due to its hydrophobic properties, the body 90 will block the liquid transport by the widened portion 88. When the sample liquid in receiving chamber 20 is subjected to a pressure, the liquid is pressed into the widened portion 88 and thus into the porosities of the hydrophobic insert body 90.

In the process, the porous body 90 has sample liquid flowing therethrough until the liquid reaches the region of the distributor channels 24 joining the widened channel portion 88 and arranged behind the insert body 90 when viewed in the flow direction. From then on, the further transport of the liquid is performed by capillary forces. Since the hydrophobic insert body 90 on its surfaces is wetted by the sample liquid as a result of the pressure acting on the latter, the liquid flow through capillary forces is maintained. Thus, in this manner, a valve function is realized by liquid control (pressure control of the sample liquid).

Figure 8:
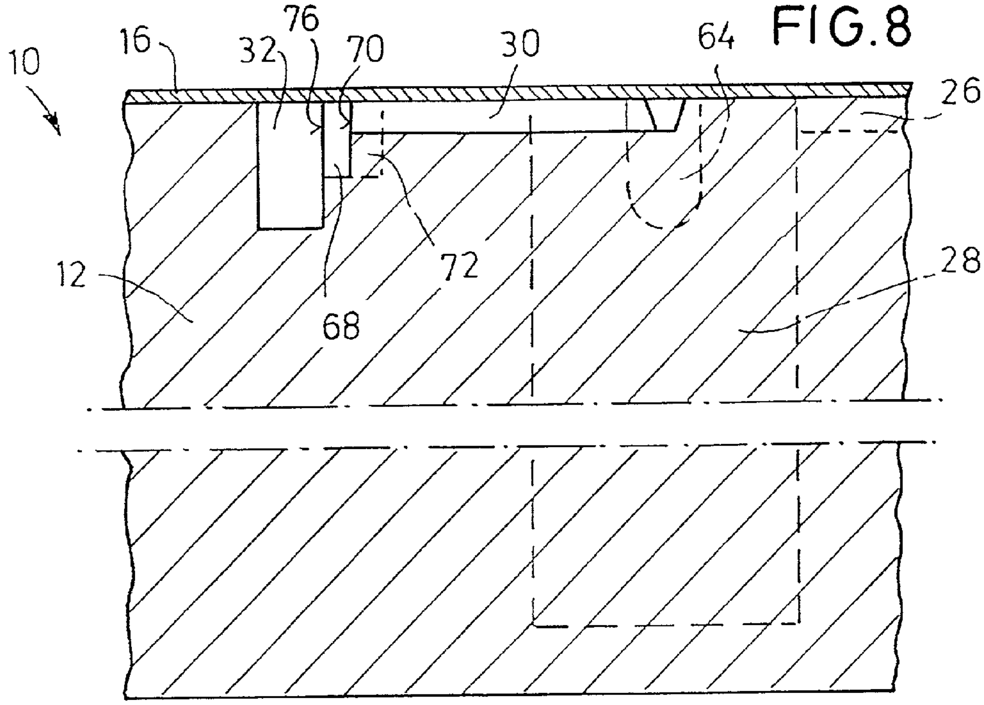

FIGS. 11 and 12 show a further alternative valve configuration 86'. The underlying thought in this valve configuration 86' is the one described in connection with the widened portions 68 (cf. FIGS. 5 and 8). Thus, also in this configuration 86', the distributor channel 24 includes a special widened channel portion 88' which in plan view and sectional view is provided in the manner shown in FIGS. 11 and 12. In the region of the entrance 92 of the portion of distributor channel 24 coming from sample receiving chamber 20, the widened portion 88' comprises a plane side face 94 which only towards the cover film 14 is delimited by a corner region. The capillary forces thus possibly generated on both sides of the entrance 92 on the underside of cover film 14 will not suffice to suck the liquid from the distributor channel 24. Thus, the liquid front advancing from the sample chamber 20 through the joining portion of the distributor channel 24, is brought to a stop at the entrance site 92. Only when pressure is applied onto the liquid of the sample receiving chamber 20, sample liquid enters the widened portion 88' and fills the same. The widened portion 88' has an outlet 92 arranged to enter the further extension of distributor channel 24. As soon as the liquid pressed into the widened portion 88' reaches the outlet 96, the further transport of the sample liquid is again performed by capillary effect.

Finally, FIGS. 13 and 14 show a configuration of a valve 86". The mechanisms and the configuration of this valve are nearly identical with the valve configuration 86'. The difference between the two valves resides in that the filling of the widened portion 88" of valve 86" is performed not by the sample liquid but by a control liquid 98 which is inert to the sample liquid. The control liquid 98 is arranged in a receiving chamber 100 which via a control channel 102 is connected to the widened portion 88'. The introducing of the control liquid 98 into the widened portion 88" can be performed by application of pressure onto the control liquid 98 on the one hand, but also by maintaining a liquid flow by use of capillary forces on the other hand. In the latter case, the measures provided are of the type described above in connection with the introducing of the sample liquid 22 into the reaction chambers 28, i.e. the entrance 104 of the control channel 102 into the widened channel portion 88" is provided in a region in which, within the widened channel portion 88", corner regions with sufficiently small rounding radii are formed, with a meniscus being generated and moving therealong. By application (cf. FIGS. 13 and 14) of control liquid into the chambers 100, the switching of valve 86" can be influenced automatically, as it were (notably from the closed into the conductive state). To have the control liquid 98 move from chamber 100 into control channel 102, use can be made again of the mechanisms and measures described above in connection with the outflow grooves of chambers 20 and 38.

As already mentioned above, the reaction chambers of the sample support can already be provided with reactive substances on the manufacturer's side, which substances are stored in the reaction chambers in dried form. Because of the small volumes of the reaction chambers, only small quantities of reactive substances are needed, which is useful for the drying process.

The introduction of the sample liquid will be performed by the user. If the cover film 16 does not extend into the regions of the upper side 14 of base plate 12 wherein the sample receiving chambers 20 are located, the latter are freely accessible so that sample liquid can be introduced in conventional manner by pipeting. The same holds true if the cover film extends across the whole upper side and is provided with openings arranged flush with the sample chambers (and the reagent liquid receiving chambers 38). For improved protection against evaporation, it is of advantage if the cover film bridges the chambers 20 and 38. In such a case, the sample liquid can be inserted by puncture of the cover film. By way of alternative, the cover film in the region of chambers 20 and 38 can be slitted, thus to be opened in the manner of a septum for introducing liquid.

With regard to the mechanisms relevant for the liquid flowing in the corner regions and along these, it should be noted here that the rounding radii referred to in the instant description are provided in the μm and sub-μm region. Further, generally, the rounding radius is advantageously smaller than the smallest dimension of the channel joined by the corner region.

The invention claimed is:

1. A sample support, comprising at least one sample receiving chamber for a sample liquid, a distributor channel for sample liquid, connected to said at least one sample receiving chamber, with at least one such distributor channel extending from said at least one sample receiving chamber, more than one reaction chamber comprising a cavity which is delimited by surfaces and is entered by an inflow channel branched off said at least one distributor channel, wherein each reaction chamber comprises a bottom surface and a side surface which forms an angle with respect to the bottom surface, and a venting opening for each reaction chamber, and valves arranged in each distributor channel and/or the venting openings of the reaction chambers or downstream thereof for causing a controlled flow of the sample liquid through the distributor channel or channels into reaction chamber or chambers, wherein each valve comprises a burst film and/or comprises a porous hydrophobic insert and/or comprises a hydrophobic inner wall and each valve can be switched hydraulically and pneumatically, respectively, from a closed condition into an open condition by external control and/or by application of pressure onto the sample liquid or the as bearing against the valve and each distributor channel and each inflow channel is dimensioned to have the liquid transport through the distributor and inflow channels effected by capillary forces, wherein, in each reaction chamber, said surfaces in the entrance region of the inflow channel which are provided for delimiting said cavity, are configured as a means for generating a capillary force causing the sample liquid to flow from the inflow channel into the reaction chamber exclusively by capillary force, and wherein said capillary force generating means is realized by a sufficiently small rounding radius in the transition region between said side surface and said bottom surface to cause sample liquid to flow along said transition regions under the effect of capillary forces.

2. The sample support according to claim 1, wherein each venting opening includes a means for preventing a further flow of sample liquid effected by capillary forces.

3. The sample support according to claim 2, wherein each of said capillary-force prevention means is provided as a widened portion of a connecting channel or venting opening, which widened portion respectively comprises a side surface with a connecting channel entering thereinto, and that the entrance region of the portion of the connecting channel extending from the reaction chamber is not delimited in the widened portion by any corner regions or only by such a small number of corner regions with rounding radii generating a capillary force that the flow of the sample liquid in the entrance region is prevented.

4. The sample support according to claim 3, wherein each venting collecting channel is arranged to extend from a reagent receiving chamber for receiving a reagent liquid, with the flow of the reagent liquid performed via the venting collecting channels by capillary forces generated within the venting collecting channels, and that, within the entrance region of each venting collecting channel into the widened portions and/or within the entrance regions where the portions of the connecting channels extending from the venting collecting channels enter the widened portions, a means is arranged for generating a capillary force for filling the widened portions.

5. The sample support according to claim 4, wherein each reagent receiving chamber comprises a bottom surface and side surfaces extending at an angular orientation thereto, and that the venting collecting channel assigned to a reagent receiving chamber is arranged to enter the reagent receiving chamber above said bottom surface, and that a means for generating a capillary force to cause reagent liquid to flow from the reagent receiving chamber into the venting collecting channel is arranged between said entrance and said bottom surface.

6. The sample support according to claim 5, wherein said capillary-force generating means is formed as an outflow groove having a cross-sectional area and shape suited to generate a flow of the reagent liquid by capillary force.

7. The sample support according to claim 6, wherein said outflow groove is provided as a trough formed in a side surface.

8. The sample support according to claim 6, wherein said outflow groove is provided as a transition region between two adjacent and mutually angled side surfaces, the transition region having a rounding radius sufficiently small to generate capillary forces causing a flow of the reagent liquid.

9. The sample support according to claim 3, wherein each venting collecting channel is arranged to extend from a reagent receiving chamber for receiving a reagent liquid, and that, within the entrance region of each venting collecting channel into the widened portions and/or within the entrance regions where the portions of the connecting channels extending from the venting collecting channels enter the widened portions, a means is arranged for generating a capillary force for filling the widened portions.

* * * * *